United States Patent [19]

Hagen et al.

[11] Patent Number: 4,715,889

[45] Date of Patent: Dec. 29, 1987

[54] QUINOLINE DERIVATIVES AND THEIR USE FOR CONTROLLING UNDESIRABLE PLANT GROWTH

[75] Inventors: Helmut Hagen, Frankenthal; Rolf-Dieter Kohler, Edingen-Neckarhausen; Jürgen Markert, Mutterstadt; Bruno Wuerzer, Otterstadt, all of Fed. Rep. of Germany

[73] Assignee: BASF Aktiengesellschaft, Ludwigshafen, Fed. Rep. of Germany

[21] Appl. No.: 530,084

[22] Filed: Sep. 7, 1983

[30] Foreign Application Priority Data

Sep. 7, 1982 [DE] Fed. Rep. of Germany ....... 3233089

[51] Int. Cl.$^4$ .................... A01N 43/42; C07D 215/48
[52] U.S. Cl. ........................ 71/94; 546/168; 546/169; 546/170; 544/363; 544/128
[58] Field of Search ................... 546/168, 169, 170; 71/94

[56] References Cited

U.S. PATENT DOCUMENTS

| | | | |
|---|---|---|---|
| 2,665,203 | 1/1954 | Emerson et al. | 71/2.5 |
| 3,818,012 | 6/1974 | Nikles | 71/94 |
| 4,009,020 | 2/1977 | Starke et al. | 71/94 |
| 4,036,963 | 7/1977 | Gialdi et al. | 546/170 |

FOREIGN PATENT DOCUMENTS

| | | |
|---|---|---|
| 359497 | 4/1978 | Austria . |
| 7410362 | 2/1975 | Netherlands . |
| 1202110 | 8/1970 | United Kingdom . |
| 1432378 | 4/1976 | United Kingdom . |
| 2080803 | 2/1982 | United Kingdom . |

OTHER PUBLICATIONS

J. Chem Soc. (1947), pp. 437–445 (cf. p. 442).
J. of Heterocycl. Chem (1974), pp. 229–230 (cf. Col. Compounds 4 & 5).

Primary Examiner—Glennon H. Hollrah
Assistant Examiner—D. B. Springer
Attorney, Agent, or Firm—Keil & Weinkauf

[57] ABSTRACT

Quinoline derivatives of the formula

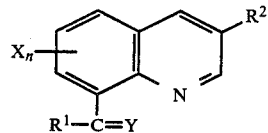

where X, n, $R^1$, $R^2$ and Y have the meanings given in the description, are used for controlling undesirable plant growth.

15 Claims, No Drawings

QUINOLINE DERIVATIVES AND THEIR USE FOR CONTROLLING UNDESIRABLE PLANT GROWTH

The present invention relates to quinoline derivatives, herbicides which contain these compounds as active ingredients, and a method of controlling undesirable plant growth with these active ingredients.

Substituted quinolines having herbicidal properties are disclosed in German Laid-Open Application DOS No. 2,322,143 and U.S. Pat. No. 2,661,276.

We have found that quinoline derivatives of the formula

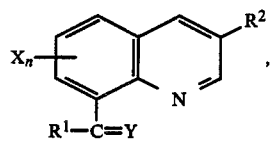

wherein

X is chlorine in position 5, 6 or 7 and n is 1, 2 or 3, Y is oxygen, sulfur, hydroximino, two hydrogen atoms, two chlorine atoms or the group =N—A—B, where A is a direct bond or methylene and B is phenyl or pyridyl, each of which is unsubstituted or substituted by chlorine, nitro, methyl, trifluoromethyl or methoxy, $R^1$ is hydrogen, halogen, cyano, or —$NR^3R^4$, where $R^3$ and $R^4$ are identical or different and are each hydrogen, $C_1$-$C_6$-alkyl, $C_2$-$C_6$-alkenyl, $C_1$-$C_6$-hydroxyalkyl, formyl, cyclohexyl, phenyl or pyridyl, or $R^3$ and $R^4$ together form a tetramethylene or pentamethylene radical, where one $CH_2$ group can be replaced by an oxygen or nitrogen atom, or $N(CH_3)$, or $R^1$ is COOH or OM, where M is one equivalent of an alkali metal or alkaline earth metal ion, hydrogen, $C_1$-$C_8$-alkyl, or phenyl which is unsubstituted or substituted by halogen, nitro, $C_1$-$C_4$-alkyl or trihalomethyl, or is $H_2NR^3R^4$, where $R^3$ and $R^4$ have the above meanings, and $R^2$ is hydrogen or $C_1$-$C_6$-alkyl which is unsubstituted or substituted in the ω-position by halogen, amino, monoalkylamino, dialkylamino or trialkylammonium where alkyl is of 1 to 4 carbon atoms, $C_1$-$C_4$-alkoxy, $C_1$-$C_4$-alkylthio, cyano, thiocyano, trialkylphosphonium where alkyl is of 1 to 4 carbon atoms or triphenylphosphonium, or is formyl, cyano, carboxyl, carbamyl or N-alkylcarbamyl or N,N-dialkylcarbamyl where alkyl is of 1 to 4 carbon atoms, or is $C_2$-$C_6$-alkenyl, or where the radical

is a nitrile group, with the proviso that $R^2$ is not hydrogen if X is chlorine in the 6-position and n is 1, have a herbicidal action and are also well tolerated by certain crops.

In formula I, Y can be oxygen, sulfur, hydroximino, two hydrogen atoms, two chlorine atoms or =N—A—B, where A is a direct bond or methylene and B is phenyl or pyridyl, each of which is unsubstituted or substituted by chlorine, nitro, methyl, trifluoromethyl or methoxy. Examples of such radicals B are 2,4-dichlorophenyl, 4-nitrophenyl, 2-trifluoromethylphenyl and pyrid-2-yl.

In formula I, $R^1$ is hydrogen, cyano, halogen, e.g. bromine, or —$NR^3R^4$, where $R^3$ and $R^4$ are identical or different and are each hydrogen, $C_1$-$C_6$-alkyl, preferably $C_1$-$C_4$-alkyl, $C_2$-$C_6$-alkenyl, preferably $C_2$-$C_4$-alkenyl, $C_1$-$C_6$-hydroxyalkyl, preferably $C_1$-$C_4$-hydroxyalkyl, formyl, cyclohexyl, phenyl or pyridyl, or where $R^3$ and $R^4$ together form a tetramethylene or pentamethylene radical in which one $CH_2$ group can be replaced by an oxygen or nitrogen atom or $N(CH_3)$. Examples of radicals of the formula —$NR^3R^4$ are amino, diethylamino, diethanolamino, N-methyl-N-n-butylamino, 4-methylpiperidinyl, cyclohexylamino, morpholin-4-yl, phenylamino and pyrrolidinyl.

In formula I, $R^1$ can furthermore be carboxyl or the group OM, where M is hydrogen, one equivalent of an alkali metal or alkaline earth metal ion, e.g. of a sodium or calcium ion, $C_1$-$C_8$-alkyl, preferably $C_1$-$C_4$-alkyl, or phenyl which is unsubstituted or substituted by halogen, nitro, $C_1$-$C_4$-alkyl or trihalomethyl, or is $H_2R^3R^4$, where $R^3$ and $R^4$ have the above meanings but are each preferably $C_1$-$C_4$-alkyl or $C_1$-$C_4$-hydroxyalkyl, e.g. methyl, ethyl, n-butyl, i-butyl, sec.-butyl, n-pentyl, n-hexyl or 2-hydroxyethyl.

In formula I, $R^2$ is hydrogen or $C_1$-$C_6$-alkyl, preferably $C_1$-$C_4$-alkyl, in particular methyl, which is unsubstituted or substituted in the ω-position by halogen, amino, monoalkylamino, dialkylamino or trialkylammonium, where alkyl is of 1 to 4 carbon atoms in each case, $C_1$-$C_4$-alkoxy, $C_1$-$C_4$-alkylthio, cyano, thiocyano, trialkylphosphonium where alkyl is of 1 to 4 carbon atoms, or triphenylphosphonium, e.g. bromomethyl, dibromomethyl, aminomethyl, methylaminomethyl, dimethylaminomethyl, tetramethylammonium, methoxymethyl, ethoxymethyl, methylthiomethyl, ethylthiomethyl, cyanomethyl, 2-cyanoethyl, thiocyanomethyl, 2-thiocyanoethyl, trimethylphosphoniummethyl or triphenylphosphoniummethyl, or $R^2$ is cyano, formyl, carboxyl, carbamyl, N-$C_1$-$C_4$-alkylcarbamyl or N,N-di-$C_1$-$C_4$-alkylcarbamyl, e.g. N-methylcarbamyl or N,N-dimethylcarbamyl, or $C_2$-$C_6$-alkenyl, preferably $C_2$-$C_4$-alkenyl, e.g. vinyl.

Preferred quinoline derivatives of the formula I are those in which X is chlorine in the 7-position, n is 1, $R^1$ is hydrogen or OM, where M is hydrogen, one equivalent of an alkali metal ion or a dialkylammonium ion where alkyl is of 1 to 4 carbon atoms, and $R^2$ is $C_1$-$C_4$-alkyl and Y is oxygen.

Novel quinoline derivatives of the formula I are those in which $R^2$ is not hydrogen if $R^1$ is hydrogen and Y is hydroxyl.

The quinoline derivatives of the formula I are obtained by reacting a compound of the formula

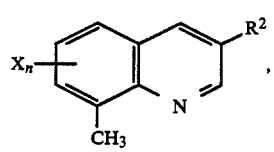

where X, n and $R^2$ have the above meanings, with a halogenating agent in the presence of a free-radical initiator at from 40° to 140° C. and, if required, converting the resulting compound of the formula

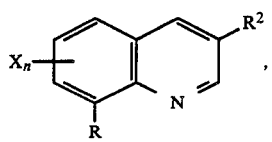

where X, n and $R^2$ have the above meanings and R is halomethyl, to the compound of the formula I, in which $R^1$ is not halogen and Y is not two hydrogen atoms or two chlorine atoms.

The halogenation of the compounds of the formula II is advantageously carried out using a halogen donor, e.g. N-chlorosuccinimide or N-bromosuccinimide, in the presence of a free-radical initiator, e.g. azoisobutyronitrile or benzoyl peroxide, in an inert solvent, e.g. chloroform, carbon tetrachloride or a chlorobenzene, at from 40° to 140° C., preferably from 60° to 100° C. This procedure gives a compound of the formula III, where R is chloromethyl or bromomethyl.

Conversion of a compound of the formula III to a compound of the formula I is advantageously carried out in a conventional manner by oxidative hydrolysis in sulfuric acid in the presence of nitric acid.

Quinoline derivatives of the formula I where $R^1$ is OM, M is hydrogen, Y is oxygen, and X, n and $R^2$ have the above meanings are obtained by reacting a compound of the formula

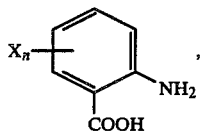

where X and n have the above meanings, with an aldehyde of the formula

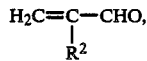

where $R^2$ has the above meanings.

Synthesis of quinolinecarboxylic acids by subjecting an anthranilic acid to a Skraup cyclization reaction is known (Monatsh. 2, (1981), 518). However, the yields are frequently low, especially in the case of 8-quinoline carboxylic acids; this is due to partial decarboxylation under the reaction conditions (Gazz. Chim. Ital., 16, (1887), 366).

It is therefore surprising that reactions of compounds of the formula IV with unsaturated aldehydes of the formula V give 8-quinolinecarboxylic acids of the formula I in good yield and purity. The reaction can be carried out in the presence of a strong mineral acid, e.g. hydrochloric acid, phosphoric acid or sulfuric acid. A preferred acid is 35–95, preferably 40–70, % strength by weight sulfuric acid. The reaction is carried out at from 80° to 160° C., preferably from 100° to 150° C.

Quinoline derivatives of the formula I in which Y is oxygen are obtained by treating the corresponding dichloro compound with a strong acid, e.g. concentrated sulfuric acid or concentrated hydrochloric acid, at from 50° to 150° C.

Quinoline derivatives of the formula I in which Y is sulfur are obtained by reacting the corresponding nitrile with hydrogen sulfide in a basic solvent, preferably pyridine.

Quinoline derivatives of the formula I in which Y is hydroximino are obtained by heating the corresponding aldehyde with hydroxylamine at from 50° to 150° C. If, instead of the free hydroxylamine, hydroxylamine hydrochloride or hydroxylamine sulfate is used, a base has to be added. Suitable bases are sodium carbonate, sodium bicarbonate and sodium hydroxide and the corresponding potassium compounds.

Quinoline derivatives of the formula I in which Y is =N—A—B are obtained by heating the corresponding aldehyde and a compound $H_2N$—A—B in a solvent, such as an alcohol or an aliphatic ether, which can be cyclic, at from 50° to 150° C.

Quinoline derivatives of the formula I in which $R^1$ is cyano are obtained by reacting the corresponding chloro compound with potassium cyanide or sodium cyanide in a solvent, e.g. dimethylformamide or dimethylsulfoxide, at from 100° to 200° C. in the presence of a little potassium iodide.

The compounds of the formula I in which $R^1$ is —$NR^3R^4$ are obtained by reacting the appropriate amide with the appropriate chloro compound at from 30° to 100° C. in the presence or absence of a solvent, such as an alcohol, an ether, or dimethylsulfoxide.

The compounds of the formula I in which $R^1$ is —$ON^{\oplus}H_2R^3R^4$ are obtained by reacting the corresponding carboxylic acid with an amine, for example in an alcohol, dimethylformamide or dimethylsulfoxide, at from 50° to 150° C.

The compounds of the formula I in which $R^1$ is carboxyl are obtained, for example, by hydrolysis of the corresponding nitrile with concentrated sulfuric acid.

The compounds of the formula I in which $R^1$ is OH are obtained by reacting the corresponding chloro compound with sodium hydroxide or potassium hydroxide.

Quinoline derivatives of the formula I in which $R^2$ is bromomethyl or dibromomethyl are obtained by reacting a compound of the formula

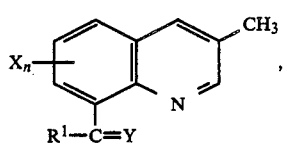

where X, n, $R^1$ and Y have the above meanings, with a bromine donor, e.g. N-bromosuccinimide. The reaction is carried out under the conditions described for the halogenation of the compounds of the formula II.

The Examples which follow illustrate the preparation of the quinoline derivatives of the formula I.

EXAMPLE 1

8-bromomethyl-7-chloro-3-methylquinoline
(compound no.1)

48 g of 7-chloro-3,8-dimethylquinoline, 89 g of N-bromosuccinimide and 0.5 g of azobisisobutyronitrile in 950 g of carbon tetrachloride were stirred for 24 hours at 76° C., after which the mixture was cooled, the precipitated succinimide was filtered off under suction and the filtrate was evaporated to dryness under reduced pressure. The residue was suspended in methanol and once again filtered off under suction.

Yield: 30 g (56% of theory); m.p. 140° C. (from ethanol).

EXAMPLE 2

7-chloro-3-methylquinoline-8-carboxylic acid (compound no.2)

10 g of a 65% strength nitric acid were added dropwise to a solution of 13 g of 8-bromomethyl-7-chloro-3methylquinoline in 100 g of 70% strength sulfuric acid at 100° C. The mixture was stirred for 4 hours at this temperature, after which the reaction solution was poured onto ice and neutralized with concentrated sodium hydroxide solution. The precipitate was filtered off under suction, washed with water and dried.

Yield: 5 g (45% of theory); m.p. 244° C. (from dimethylformamide).

EXAMPLE 3

7-chloro-3-methylquinoline-8-carboxylic acid (compound no.2)

14 g of methacrolein were added dropwise to a mixture of 17 g of 6-chloroanthranilic acid and 19 g of sodium m-nitrobenzenesulfonate in 100 g of 57% strength sulfuric acid at 100° C. When the addition was complete, the reaction mixture was stirred for 1 hour at 130° C. and then poured into 450 g of water, and the mixture was filtered under suction. The filtrate was brought to pH 2-3 with concentrated sodium hydroxide solution, while cooling. The precipitated solid was filtered off under suction, washed with water and dried.

Yield: 16 g (72% of theory); m.p. 244° C. (from dimethylformamide).

EXAMPLE 4

7-chloro-3-ethylquinoline-8-carboxylic acid (compound no.3)

16.8 g of ethylacrolein were added dropwise, at 100° C., to a solution of 17 g of 6-chloroanthranilic acid and 19 g of sodium m-nitrobenzenesulfonate in 200 g of 57% strength sulfuric acid. The reaction solution was stirred for 1 hour at 130° C., after which it was diluted with 450 g of water, and the pH was brought to 2-3 with concentrated sodium hydroxide solution, while cooling. The precipitated solid was filtered off under suction, washed with water and dried.

Yield: 15 g (64% of theory); m.p. 200° C. (from ethanol).

EXAMPLE 5

5-chloro-3-methylquinoline-8-carboxylic acid (compound no.4)

14 g of methacrolein were added dropwise, at 100° C., to a solution of 17 g of 4-chloroanthranilic acid and 19 g of sodium m-nitrobenzenesulfonate in 200 g of 57% strength sulfuric acid. The mixture was stirred for 1 hour at 130° C., after which it was diluted with 450 g of water and filtered under suction while hot. The pH was brought to 2-3 with concentrated sodium hydroxide solution, while cooling. The precipitated solid was filtered off under suction, washed with water and dried.

Yield: 14 g (64% of theory); m.p. 165° C.

EXAMPLE 6

5,7-dichloro-3-methylquinoline-8-carboxylic acid (compound no.5)

14 g of methacrolein were added dropwise, at 100? C, to a solution of 20.6 g os 4,6-dichloroanthranilic acid and 19 g of sodium m-nitrobenzenesulfonate in 200 g of 57% strength sulfuric acid. The mixture was stirred for 1 hour at 130° C., after which it was diluted with 450 g of water and filtered under suction while hot. The pH was brought to 2-3 with concentrated sodium hydroxide solution, while cooling with ice. The precipitated solid was filtered off under suction, washed with water and dried.

Yield: 13 g (50% of theory); m.p. 220° C.

The following compounds of the formula I can be prepared by a similar method:

| Compound No. | $X_n$ | Y | $R^1$ | $R^2$ | m.p. (°C.) |
|---|---|---|---|---|---|
| 6 | 7-Cl | 0 | $CH_3O$ | $CH_3$ | |
| 7 | 7-Cl | 0 | $C_2H_5O$ | $CH_3$ | |
| 8 | 7-Cl | 0 | $n\text{-}C_4H_9O$ | $CH_3$ | |
| 9 | 7-Cl | 0 | $n\text{-}C_5H_{11}O$ | $CH_3$ | |
| 10 | 7-Cl | 0 | $n\text{-}C_6H_{13}O$ | $CH_3$ | |
| 11 | 7-Cl | 0 | $OCH_3$ | $C_2H_5$ | |
| 12 | 7-Cl | 0 | $OC_2H_5$ | $C_2H_5$ | |
| 13 | 7-Cl | 0 | $O^{\ominus}Na^{\oplus}$ | $CH_3$ | |
| 14 | 7-Cl | 0 | $O^{\ominus}Na^{\oplus}$ | $C_2H_5$ | |
| 15 | 7-Cl | 0 | $O^{\ominus}\overset{\oplus}{N}H_3[(CH_2)_2OH]$ | $CH_3$ | |
| 16 | 7-Cl | 0 | $O^{\ominus}\overset{\oplus}{N}H_2[(CH_2)_2OH]_2$ | $CH_3$ | |
| 17 | 7-Cl | 0 | $O^{\ominus}\overset{\oplus}{N}H_3[(CH_2)_2OH]$ | $C_2H_5$ | |
| 18 | 7-Cl | 0 | $O^{\ominus}\overset{\oplus}{N}H_2[(CH_2)_2OH]_2$ | $C_2H_5$ | |
| 19 | 7-Cl | 0 | $NH_2$ | $CH_3$ | |
| 20 | 7-Cl | 0 | $N(C_2H_5)_2$ | $CH_3$ | |

-continued

| Compound No. | $X_n$ | Y | $R^1$ | $R^2$ | m.p. (°C.) |
|---|---|---|---|---|---|
| 21 | 7-Cl | 0 | —N(piperazinyl)N—CH$_3$ | CH$_3$ | |
| 22 | 7-Cl | 0 | N(CH$_2$—CH$_2$OH)$_2$ | CH$_3$ | |
| 23 | 7-Cl | 0 | N(CH$_3$)(n-C$_4$H$_9$) | CH$_3$ | |
| 24 | 7-Cl | 0 | OH | CH$_2$Br | 220 |
| 25 | 7-Cl | 0 | OCH$_3$ | CH$_2$Br | |
| 26 | 7-Cl | 0 | OC$_2$H$_5$ | CH$_2$Br | |
| 27 | 5,7-Cl$_2$ | 0 | OCH$_3$ | CH$_3$ | |
| 28 | 5,7-Cl$_2$ | 0 | OC$_2$H$_5$ | CH$_3$ | |
| 29 | 5,7-Cl$_2$ | 0 | n-C$_4$H$_9$O | CH$_3$ | |
| 30 | 5,7-Cl$_2$ | 0 | n-C$_5$H$_{11}$O | CH$_3$ | |
| 31 | 5,7-Cl$_2$ | 0 | n-C$_6$H$_{13}$O | CH$_3$ | |
| 32 | 5,7-Cl$_2$ | 0 | CH$_3$O | C$_2$H$_5$ | |
| 33 | 5,7-Cl$_2$ | 0 | C$_2$H$_5$O | C$_2$H$_5$ | |
| 34 | 5,7-Cl$_2$ | 0 | O$^\ominus$Na$^\oplus$ | CH$_3$ | |
| 35 | 5,7-Cl$_2$ | 0 | O$^\ominus$Na$^\oplus$ | C$_2$H$_5$ | |
| 36 | 5,7-Cl$_2$ | 0 | O$^\ominus$NH$_3^\oplus$[(CH$_2$)$_2$OH] | CH$_3$ | |
| 37 | 5,7-Cl$_2$ | 0 | O$^\ominus$NH$_2^\oplus$[(CH$_2$)$_2$OH]$_2$] | CH$_3$ | |
| 38 | 5,7-Cl$_2$ | 0 | O$^\ominus$NH$_3^\oplus$[(CH$_2$)$_2$OH] | C$_2$H$_5$ | |
| 39 | 5,7-Cl$_2$ | 0 | O$^\ominus$NH$_2$[(CH$_2$)$_2$OH]$_2$ | C$_2$H$_5$ | |
| 40 | 5,7-Cl$_2$ | 0 | NH$_2$ | CH$_3$ | |
| 41 | 5,7-Cl$_2$ | 0 | N(C$_2$H$_5$)$_2$ | CH$_3$ | |
| 42 | 5,7-Cl$_2$ | 0 | —N(piperazinyl)N—CH$_3$ | CH$_3$ | |
| 43 | 5,7-Cl$_2$ | 0 | N(CH$_2$CH$_2$OH)$_2$ | CH$_3$ | |
| 44 | 5,7-Cl$_2$ | 0 | N(CH$_3$)(n-C$_4$H$_9$) | CH$_3$ | |
| 45 | 5,7-Cl$_2$ | 0 | OH | CH$_2$Br | |
| 46 | 5,7-Cl$_2$ | 0 | OCH$_3$ | CH$_2$Br | |
| 47 | 5,7-Cl$_2$ | 0 | OC$_2$H$_5$ | CH$_2$Br | |
| 48 | 7-Cl | 0 | OH | COOH | 260 |
| 49 | 7-Cl | 0 | OH | n-C$_3$H$_7$ | 200 |
| 50 | 7-Cl | 0 | OH | CH$_2$P$^\oplus$(C$_6$H$_5$)$_3$Br$^\ominus$ | 260 |
| 51 | 7-Cl | 0 | OH | H | 244 |

The compounds of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives. such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below:

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 3 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 2 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 24 is intimately mixed with 97 parts by weight of particulate kaolin. A dust is obtained containing 3% by weight of the active ingredient.

VII. 30 parts by weight of compound no. 49 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 5 is intimately mixed with 2 parts of the calcium salt of dodecylbenzenesulfonic acid, 8 parts of a fatty alcohol polyglycol ether, 2 parts of the sodium salt of a phenolsulfonic acid-ureaformaldehyde condensate and 68 parts of a paraffinic mineral oil. A stable oily dispersion is obtained.

The active ingredients or agents may be applied preor postemergence. In the case of especially sensitive crop plants, application techniques may be used in which the herbicidal agents are sprayed from suitable equipment in such a manner that the leaves of the sensitive crop plants are if possible not touched, and the agents reach the soil or the unwanted plants growing beneath the crop plants (post-directed, lay-by treatment).

The amount of active ingredient applied depends on the time of the year, the objective to be achieved, the plants to be combated, and the growth stage of the plants, and varies from 0.05 to 5 kg/ha, but is preferably from 0.5 to 3 kg/ha.

The herbicidal influence of compounds of the formula I is demonstrated in greenhouse experiments.

The vessels employed were plastic flowerpots having a volume of 300 $cm^3$, and which were filled with a sandy loam containing about 1.5% humus. The seeds of the test plants were sown shallow, and separately, according to species. Rice was grown in a peat-enriched substrate to ensure better growth. For the preemergence treatment, the active ingredients were applied to the surface of the soil immediately after the seeds had been sown. The compounds were emulsified or suspended in water as vehicle, and sprayed through finely distributing nozzles. The application rates were, for example, 0.5 and 2.0 kg of active ingredient per hectare.

After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown separately as seedlings and transplanted to the experiment vessels a few days before treatment. No covers were placed on the pots in this treatment method. The application rates for postemergence treatment were, for example, 0.5, 1.0 and 3.0 kg of active ingredient per hectare.

The pots were set up in the greenhouse - species from warmer areas at from 20° to 35° C., and species from moderate climates at 10° to 20° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the greenhouse experiments were *Apium graveolens, Avena sative, Brassica napus, Beta vulgaris, Cassia tora, Centaurea cyanus, Daucus carota, Galium aparine, Hordeum vulgare,* Ipomoea spp., *Lamium amplexicaule, Mentha piperita, Oryza sativa, Secale cereale, Solanum nigrum, Triticum aestivum,* Veronica spp., *Veronica persica,* and *Zea mays.*

The following substituted quinoline derivatives were used as comparative agent:

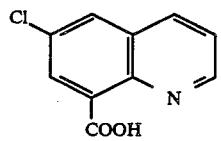

(A; U.S. Pat. No. 4,036,963)

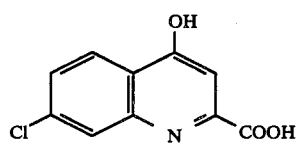

(B; U.S. Pat. No. 2,661,276)

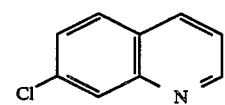

(C; German Laid-Open Application DE-OS 23 22 143).

The application rates correspond to those used for the compounds according to the invention in each of the experiments.

Preemergence application:

Compound no. 2, for example at 0.5 kg/ha, has a good herbicidal action on typical weeds and on crop plant species as representatives of the Umbelliferae family. At the same time the compound is well tolerated by a number of agricultural crops. The same applies to compound no. 3, which, at 2.0 kg/ha, also selectively combats unwanted plants in crops.

Postemergence application:

For example compound no. 2, at 05, 1.0 and 3.0 kg/ha, combats unwanted plants well without damaging crop plants such as oats, rapeseed and barley. Compound no. 24 is, at 0.5 kg/ha, particularly effective on Galium aparine and is selective in sugarbeets, Indian corn and wheat. Compound no. 3 has a good action on broadleaved weeds, rapeseed and barley tolerating 0.5 kg/ha, and oats tolerating 3.0 kg/ha. Further, for instance compounds nos. 4 and 5 exhibit a considerable herbicidal action at 3.0 kg/ha.

The compounds A, B and C employed as comparative agents have a herbicidal action which is far inferior to that of the quinoline derivatives of the formula I.

In view of the good tolerance of the active ingredients according to the invention, or agents containing them, by numerous broadleaved and other crops, and the numerous application methods possible, they may be used in a large number of crops for removing unwanted plant growth.

The following crops may be mentioned by way of example:

| Botanical name | Common name |
| --- | --- |
| *Allium cepa* | onions |
| *Ananas comosus* | pineapples |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Brassica napus* var. *napus* | rape seed |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cynodon dactylon* | Bermudagrass in turf and lawns |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Linum usitatissimum* | flax |
| *Lycopersicon lycopersicum* | tomatoes |
| *Malus* spp. | apple trees |
| *Manihot esculenta* | cassava |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | |
| *Pennisetum glaucum* | |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |

| Botanical name | Common name |
| --- | --- |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the compounds according to the invention may be mixed and applied together with numerous representatives of other herbicidal or growth-regulating active ingredient groups. Examples of suitable mixture components are diazines. 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, etc.

Particularly suitable mixture components are urea derivatives such as 3-(3-chloro-4-methylphenyl)-1,1-dimethylurea or 3-(4-isopropylphenyl)-I,1-dimethylurea. These ureas are preferably combined with quinoline derivatives of the formula I in which X is chlorine in the 7-position, n is 1, $R^1$ is hydrogen or OM, M being hydrogen, one equivalent of an alkali metal ion or a dialkylammonium ion where alkyl is of 1 to 4 carbon atoms, $R^2$ is $C_1$-$C_4$-alkyl and Y is oxygen.

A very good herbicidal action is exhibited for example by compositions containing 3-methyl-7-chloro-8-carboxyquinoline or 3-ethyl-7-chloro-8-carboxyquinoline and one of the two ureas mentioned above.

The following active ingredients are also suitable as mixture components:

3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salt
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-d
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazion-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethyl-aniline
N-n-propyl-N-β-chloroethyl-2,6-dinitro-4-trifluoromethyl-aniline
N-n-propyl-N-cyclopropylmethyl-2,6-dinitro-4-trifluoromethyl-aniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
N,N-di-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
isopropyl N-3-chlorophenylcarbamate
butyl-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
(3-(N'-methyl-N'-phenylcarbamoyloxy)-phenyl)-methyl-N-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-ethylhexahydro-1-H-azepine-1-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
alpha,alpha-dichloropropionic acid, sodium salt
alpha,alpha-dichlorobutyric acid, sodium salt
alpha,alpha,beta,beta-tetrafluoropropionic acid, sodium salt
alpha-methyl-alpha,beta-dichloropropionic acid, sodium salt methyl alpha-chloro-beta-(4-chlorophenyl)-propionate
methyl alpha,beta-dichloro-beta-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-amimoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
2-amino-6-tert.butyl-3-methylthio-4,5-dihydro-1,2,4-triazin-5-one
2-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-isopropyl-5-bromo-6-methyluracil
3-sec.butyl-5-bromo-6-methyluracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(1-methylpropyn-2-yl)-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloroacetanilide
2,6-dimethyl-N-(4-methylpyrazol-1-yl-methyl)-2-chloroacetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3-dimethyl-N-isopropyl-2-chloroacetanilide
2,6-diethyl-N-(propoxyethyl)-2-chloroacetanilide
alpha-(2-methyl-4-chlorophenoxy)-N-methoxyacetamide
2-(alpha-naphthoxy)-N,N-diethylpropionamide
2,2-diphenyl-N,N-dimethylacetamide
alpha-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyltrifluoromethanesulfone anilide
5-acetamido-4-methyltrifluoromethanesulfone anilide
2-propionylamino-4-methyl-5-chlorothiazole
0-(methylsulfonyl)-glycolic acid N-ethoxymethyl-2,6-dimethylanilide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione 2-(3-isopropylcarbamoyloxyphenyl)-4-methyl-1,2,4-oxadiazolidine-3,5-dione
2-phenyl-3,1-benzoxazinone-(4)
3-(4-bromophenyl)-3,4,5,9,10-pentaazatetracyclo-[5,4,1,0$^{2,6}$,0$^{8,1}$]-dodeca-3,9-diene
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(alpha,alpha-dimethylbenzyl)-3-(4-methylphenyl)-urea
1-phenyl-3-(2-methylcyclohexyl)-urea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-3-methyl-3-n-butylurea
1-(3-trifluoromethylphenyl)-3,3-dimethylurea
1-(alpha,alpha-tetrafluoroethoxyphenyl)-3,3-dimethylurea
1-(3-tert.butylcarbamoyloxyphenyl)-3,3-dimethylurea
1-(3-chloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2,4-dichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl alpha-naphthoxyacetate
2-(2,4-dichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
0,0-diisopropyl-5-(2-benzosulfonylaminoethyl)-phosphorodithioate
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
ammonium thiocyanate
calcium cyanamide
2-chloro-4-trifluoromethyl-3'-ethoxycarbonyl-4'-nitrophenyl ether
1-(4-benzyloxyphenyl)-3-methyl-3-methoxyurea
2-[1-(2,5-dimethylphenyl)-ethylsulfonyl]-pyridine-N-oxide
N-benzyl-N-isopropyl-trimethylacetamide
methyl 2-[4-(4'-chlorophenoxymethyl)-phenoxy]-propionate
ethyl 2-[4-(5'-bromopyridyl-2-oxy)-phenoxy]-propionate
n-butyl 2-[4-(5'-iodopyridyl-2-oxy)-phenoxy]-propionate
2-chloro-4-trifluoromethylphenyl-3'-(2-fluoroethoxy)-4'-nitrophenyl ether
2-chloro-4-trifluoromethylphenyl-3-(ethoxycarbonyl)-methylthio-4-nitrophenyl ether
2,4,6-trichlorophenyl-3-(ethoxycarbonyl)-methylthio-4-nitrophenyl ether
2-[1-(N-ethoxamino)-butylidene]-5-(2-ethylthiopropyl)-3-hydroxy-cyclohex-2-en-1-one (salts)
2-[1-(N-ethoxamino)-butylidene]-5-(2-phenylthiopropyl)-3-hydroxy-cyclohex-2-en-1-one (salts)
ethyl 4-[4-(4'-trifluoromethyl)-phenoxy]-pentene-2-carboxylate
2-chloro-4-trifluoromethyl-3'-methoxycarbonyl-4'-nitrophenyl ether
2,4-dichlorophenyl-3'-carboxy-4-nitrophenyl ether (salts)
4,5-dimethoxy-2-(3-alpha,alpha,beta-trifluoro-beta-bromoethoxyphenyl)-3-(2H)-pyridazinone
2,4-dichlorophenyl-3'-[2-(2-ethoxy-ethoxy)-ethoxy]-4'-nitrophenyl ether
2,3-dihydro-3,3-dimethyl-5-benzofuranyl-ethane sulfonate N-[4-methoxy-6-methyl-1,3,5-triazin-2-yl-aminocarbonyl]-2-chlorobenzene sulfonamide
1-(3-chloro-4-ethoxyphenyl)-3,3-dimethylurea
ethyl 2-methyl-4-chlorophenoxy-thioacetate
2-chloro-3,5-diiodo-4-acetoxy-pyridine
1(-4-[2-(4-methylphenyl)-ethoxy]-phenyl)-3-methyl-3-methoxyurea
2,6-dimethyl-N-(pyrazol-methylenoxymethyl)-2-chloroacetanilide
2-methyl-6-ethyl-N-(pyrazolyl-methylenoxymethyl)-2-chloroacetanilide
alpha-2,4-dichlorophenoxy-propionic acid)-(3-methoxycarbonyl-amino)-anilide
1-(alpha-2-bromo-4-chlorophenoxypropionic acid)-3-(0-methylcarbamoyl)-anilide
2-methyl-6-ethyl-N-(pyrazolyl-ethylenoxymethyl)-2-chloro-acetanilide
2-(3-trifluoromethylphenyl)-4H-3,1-benzoxazin-4-one
2-(3-pentafluoroethoxyphenyl)-4H-3,1-benzoxazin-4-one
2-(3-trifluoromethylthio-phenyl)-4H-3,1-benzoxazin-4-one
2-(3-difluorochloromethoxyphenyl)-4H-3,1-benzoxazin-4-one
5-nitro-2-(3-trifluoromethyl-phenyl)-4H-3,1-benzoxazin-4-one
5-chloro-2-(3-trifluoromethoxyphenyl)-4H-3,1-benzoxazin-4-one
5-chloro-2-(3-alpha,alpha,beta,beta-tetrafluoroethoxyphenyl)-4H-3,1-benzoxazin-4-one
5-fluoro-2-(3-alpha,alpha,beta,beta-tetrafluoroethoxyphenyl)-4H-3,1-benzoxazin-4-one
5-chloro-2-(4-difluorochloromethoxyphenyl)-4H-3,1-benzoxazin-4-one
5-fluoro-2-(4-difluorochloromethoxyphenyl)-4H-3,1-benzoxazin-4-one
5-fluoro-2-phenyl-4H-3,1-benzoxazin-4-one
5-fluoro-2-(3-difluoromethoxyphenyl)-4H-3,1-benzoxazin-4-one
5-chloro-2-phenyl-4H-3,1-benzoxazin-4-one
methyl N-3-chloro-4-isopropylphenyl-thiolcarbamate
6-methyl-3-methoxy-5,6-dihydro-1,2,4,6-thiatriazin-5-one-1,1-dioxide, sodium salt
6-methyl-3-ethoxy-5,6-dihydro-1,2,4,6-thiatriazin-5-one-1,1-dioxide
5-amino-4-chloro-2-phenyl-3(2H)-pyridazinone
5-amino-4-bromo-2-phenyl-3(2H)-pyridazinone
5-methylamino-4-chloro-2-(3-trifluoromethylphenyl)-3(2H)-pyridazinone
5-methylamino-4-chloro-2-(3-alpha,alpha,beta,beta-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
1-[3'-(2''-chloro-4''-trifluoromethylphenoxy)]-phenyl-4,5-di-methoxy-pyridazin-6-one
1-[4'-(3''-trifluoromethyl-phenoxy)]-phenyl-4,5-dimethoxy-pyridazin-6-one
methyl N-[4-(4'-methoxy-phenoxy)-3-chlorophenyl]-carbamate
methyl N-[4-(4'-difluoromethoxy-phenoxy)-3-chlorophenyl]-thio-carbamate
methyl N-[4-(4'-difluoromethoxy-phenoxy)-phenyl]thio-carbamate
1-[4-(4'-methylphenylpropyl)-phenyl]-3-methyl-3-methoxyurea
1-[3-(4'-chlorophenyl-propyl)-phenyl]-3-methyl-3-methoxyurea
1-[4-(3-phenyl-2-methyl-propyl)-phenyl]-3-methyl-3-methoxyurea
1-[4-(3-(4'-chlorophenyl)-2-methyl-propyl)-phenyl]-3-methyl-3-methoxyurea
1-[4-(3-(4'-methylphenyl)-2-methylpropyl)-phenyl]-3-methyl-3-methoxyurea
2-[1-(N-ethyloxyamino)-butylidene]-5(4-ethylphenyl)-3-hydroxy-cyclohexen-(2)-one-(1) (salts)
2-[1-(N-ethyloxyamino)-butylidene]-5(4-fluorophenyl)-3-hydroxy-cyclohexen-(2)-one-(1) (salts)
2-[1-(N-ethyloxyamino)-butylidene-5-(4-chlorophenyl)-3-hydroxy-cyclohexen-(2)-one-(1) (salts)
methyl 2'-(2,4,6-trichlorophenyl)-hydrazino-2-cyanoacrylate
2-[1-(N-ethyloxamino)-butylidene]-5-(1,3,3-trimethyl-cyclohexen-1-yl-2)-3-hydroxy-cyclohexen-(2)-one-(1) (salts)
2-[1-(N-ethyloxamino)-butylidene]-5-(2,4,4-trimethyl-cyclohexen-1-yl-3)-3-hydroxy-cyclohexen-(2)-one-(1) (salts)
2-[1-(N-3-chloroallyl-oxamino)-butylidene]-5-(1-methyl-cyclohex-1-en-4-yl)-3-hydroxy-cyclohexen-(2)-one-(1) (salts)
3-isobutoxy-5-methyl-4-methoxycarbonyl-pyrazole
5-amino-1-(2,4,6-trichlorophenyl)-4-cyano-pyrazole
5-amino-1-(2,4,6-tribromophenyl)-4-cyano-pyrazole
5-amino-1-(2,4,6-trichlorophenyl)-4-methoxycarbonyl-pyrazole
5-amino-(2,4-dichloro-6-bromophenyl)-4-methoxycarbonyl-pyrazole
5-amino-(2,6-dichloro-4-bromophenyl)-4-methoxycarbonyl-pyrazole
5-chloro-2-(3-trifluoromethyl-phenyl)-4H-3,1-benzoxazin-4-one
5-fluoro-2-(3-trifluoromethyl-phenyl)-4H-3,1-benzoxazin-4-one
2-(3-tetrafluoroethoxyphenyl)-4H-3,1-benzoxazin-4-one
5-chloro-2-(4'-fluorophenyl)-4H-3,1-benzoxazin-4-one
5-fluoro-2-(4'-fluorophenyl)-4H-3,1-benzoxazin-4-one
5-fluoro-2-(3'-fluorophenyl)-4H-3,1-benzoxazin-4-one
5-chloro-2-(3'-fluorophenyl)-4H-3,1-benzoxazin-4-one
5-chloro-2-(3'-difluorochlormethylphenyl)-4H-3,1-benzoxazin-4-one
5-fluoro-2-(3'-difluorochlormethylphenyl)-4H-3,1-benzoxazin-4-one
6-methyl-3-methoxy-5-(4'-nitrophenoxy)-6H-1,2,4,6-thiatriazine-1,1-dioxide
6-methyl-3-methoxy-5-(propargyloxy-6H-1,2,4,6-thiatriazine-1,1-dioxide
6-methyl-3-methoxy-5-(2,4-dichlorobenzoxy)-6H-1,2,4,6-thiatriazine-1,1-dioxide
2-(2',4'-dichlorophenoxy)-2-fluoropropionic acid (salts, esters)
butyl 2-[4-(5'-trifluoromethylpyridyl-2-oxy)-phenoxy]-propionate
2-[4-(3'-chloro-5'-trifluoromethylpyridyl-2-oxy)-phenoxy]-propionic acid (salts, esters)
pentyl 2-[4-(6-chloroquinoxalyl-2-oxy)-phenoxy]-propionate
methyl 2-[4-(6-chloroquinoxalyl-2-oxy)-phenoxy]-propionate
2-[4-(6-chlorobenzthiazolyl-2-oxy)-phenoxy]-propionic acid (salts, esters)
2-[4-(6-chlorobenzoxazolyl-2-oxy)-phenoxy]-propionic acid (salts, esters)
1-[5-(3-fluorobenzylthio)-thiadiazolyl-2]-1-methylurea
2-methoxycarbonyl-N-(3,5-dimethylpyrimidinyl-2-aminocarbonyl)-benzole sulfonamide alpha-(3,5,6-trichloropyrid-2-yl-oxy)-acetic acid (salts, esters)
alpha-(4-amino-3,5-dichloro-6-fluoro-pyrid-2-yl-oxy)-acetic acid (salts, esters)
S-[N-(4-chlorophenyl)-N-isopropyl-carbamoyl-methyl]-0,0-dimethyl-dithiophosphate
ammonium-(3-amino-3-carboxy-propyl)-methylphosphinate
(hydroxy)-(methyl)-phosphinyl-L-alpha-aminobutyryl-L-alanyl, sodium salt
4-trifluoromethyl-diphenyl ether
2-(3,5-dichlorophenyl)-2-(2'2'2'-trichloroethyl)-oxirane
2,4-diamino-5-methylthio-6-chloropyrimidine
N-(4-ethylthio-2-trifluoromethyl-phenyl)-methylsulfonamide
3-methoxy-4-methyl-5(3-methyl-2-butenyloxy)-1,2-di(-hydroxymethyl)-benzole
2-(3,5-dimethylphenoxy)-2-(1,2,4-triazolyl-1)-acetic acid-N-tert-butylamide
2-(3,5-dichlorophenoxy)-2-(1,2,4-triazolyl-1)-acetic acid-N-tert-butylamide
3,7-dichloro-8-quinolinecarboxylic acid (salts, esters)
5-(2-chloro-4-trifluoromethyl-phenoxy)-N-(1-methoxycarbonylethoxy)-benzamide
N-[3-(1-ethyl-1-methylpropyl)-isoxazolyl-5]-2,6-dimethoxybenzamide
2'-methoxyethyl-2-[5-(2-chloro-4-trifluoromethyl-phenoxy)-2-nitrophenoxy]-propionate
methyl-6-(4-isopropyl-4-methyl-5-oxo-2-imidazolin-2-yl)-3-methylbenzoate
methyl-6-(4-isopropyl-4-methyl-5-oxo-2-imidozin-2-yl)-4-methylbenzoate
benzyltrimethylammonium chloride
1-[alpha-(4-trifluoromethyl-phenoxy)-phenoxy-propionic acid]-3—(0-methylcarbamoyl)-anilide
1-dodecyl-cycloheptan-2-one
N-[2-chloro-4-methylsulfonyl-phenyl]-chloromethanesulfonamide
N-[2-bromo-4-ethylsulfonyl-phenyl]-chloromethanesulfonamide
N-[2,3-dichloro-4-(ethylsulfonyl)-phenyl]-chloromethanesulfonamide
2-[1-(N-ethoxyamino)-pyropylidene]-5-(pyrid-3-yl)-3-hydroxy-cyclohex-2-en-1-one (salts)
2,4,5-trichlorophenoxyacetic acid (salts, esters, amides)
2-[1-(N-ethoxyamino)-butylidene]-5-(tetrahydropyran-3-yl)-3-hydroxy-cyclohex-2-en-1-one (salts)
2-[1-(N-ethoxyamino)-butylidene]-5-(4-methyl-tetrahydropyran-3-yl)-3-hydroxy-cyclohex-2-en-1-one (salts)
2-[1-(N-ethoxyamino)-butylidene]-5-(tetrahydrothiopyran-3-yl)-3-hydroxy-cyclohex-2-en-1 -one (salts)
2-[1-(N-ethoxyamino)-propylidene]-5-(pyrid-3-yl)-3-hydroxy-cyclohex-2-en-1-one (salts)
2-[1-(N-allyloxyamino)-propylidene]-5-(pyrid-3-yl)-3-hydroxy-cyclohex-2-en-1-one
2-[1-(N-ethoxyamino)-butylidene]-5-(pyrid-3-yl)-3-hydroxy-cyclohex-2-en-1-one (salts)
2-[1-(N-allyloxyamino)-butylidene]-5-(pyrid-3-yl)-3-hydroxy-cyclohex-2-en-1-one (salts)
2-[4,5-dihydro-4-methyl-4-isopropyl-5-oxo-1H-imidazol-2-yl]-3-quinolinecarboxylic acid
2-[4,5-dihydro-4-methyl-4-isopropyl-5-oxo-1H-imidazol-2-yl]-nicotinic acid, isopropylamine salt
2-chloro-2'-methyl-6'-ethyl-N-(N'-1-methoxycarbonyl)-ureidomethylacetanilide
2-chloro-2'-6'-diethyl-N-(N'-1-methoxycarbonyl)-ureidomethylacetanilide
2-chloro-2'-6'-dimethyl-N-(N'-1-methoxycarbonyl)-ureidomethylacetanilide
2-chloro-6-nitro-3-phenoxy-aniline
N-phosphonomethyl-glycine, trimethyl-sulfonium salt
5-(2-chloro-4-trifluoromethyl-phenoxy)-2-nitro-N-methanesulfonyl-benzamide
5-(3-chloro-4-trifluoromethyl-phenoxy)-2-nitro-benzoic acid-1-ethoxycarbonyl-ethyl)-ester.

It may also be useful to apply the novel compounds, either on their own or combined with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A quinoline derivative of the formula

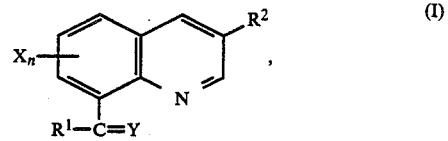

wherein

X is chlorine in position 5 or 7 and n is 1 or 2, Y is oxygen, $R^1$ is $—NR^3R^4$, where $R^3$ and $R^4$ are identical or different and are each hydrogen, $C_1–C_6$-alkyl, $C_2–C_6$-alkenyl, $C_1–C_6$-hydroxyalkyl, formyl, cyclohexyl, phenyl or pyridyl, or $N(CH_3)$, or $R^1$ is OM, where M is one equivalent of an alkali metal or alkaline earth metal ion, hydrogen, or is $H_2NR^3R^4$, where $R^3$ and $R^4$ have the above meanings, and $R^2$ is hydrogen, or $C_1–C_4$-alkyl which is unsubstituted or substituted in the ω-position by halogen, amino, monoalkylamino, dialkylamino or trialkylammonium where alkyl is of 1 to 4 carbon atoms, $C_1–C_4$-alkoxy, or is formyl, cyano, carboxy or $C_2–C_6$-alkenyl, with the proviso that $R^2$ is not hydrogen when

is carboxyl.

2. A quinoline derivative of the formula I as claimed in claim 1, where X is chlorine in the 7-position, n is 1, $R^1$ is OM, M denoting hydrogen, one equivalent of an alkali metal ion or a dialkylammonium ion where alkyl is of 1 to 4 carbon atoms, $R^2$ is $C_1–C_4$-alkyl and Y is oxygen.

3. 3-Methyl-7-chloro-8-carboxyquinoline.

4. A quinoline derivative of the formula I as defined in claim 1, where

X is chlorine in position 5 or 7 and n is 1 or 2, Y is oxygen, $R^1$ is $—NR^3R^4$, where $R^3$ and $R^4$ are identical or different and are each hydrogen, $C_1–C_6$-alkyl, $C_2–C_6$-alkyl, $C_2–C_6$-alkenyl, $C_1–C_6$-hydroxyalkyl or cyclohexyl, or $N(CH_3)$, or $R^1$ is OM, where M is one equivalent of an alkali metal or alkaline earth metal ion, hydrogen, or $H_2NR^3R^4$, where $R^3$ and $R^4$ have the above meanings, and $R^2$ is $C_1–C_4$-alkyl which is unsubstituted or substituted in the ω-position by halogen, or is formyl, cyano or carboxyl.

5. A quinoline derivative of the formula I as defined in claim 1, where

X is chlorine in position 5 or 7 and n is 1 or 2, Y is oxygen, $R^1$ is $-NR^3R^4$, where $R^3$ and $R^4$ are identical or different and are each hydrogen, $C_1-C_6$-alkyl, $C_2-C_6$-alkenyl, $C_1-C_6$-hydroxyalkyl or cyclohexyl, or $N(CH_3)$, or $R^1$ is OM, where M is one equivalent of an alkali metal or alkaline earth metal ion, hydrogen or $H_2NR^3R^4$, where $R^3$ and $R^4$ have the above meanings, and $R^2$ is $C_1-C_4$-alkyl which is unsubstituted or substituted in the $\omega$-position by halogen.

6. A herbicidal composition containing inert additives and an effective amount of a quinoline derivative of the formula I as defined in claim 1.

7. A process for combating the growth of unwanted plants, wherein the unwanted plants and/or their location are treated with a herbicidally effective amount of a composition as defined in claim 6.

8. A herbicidal composition containing inert additives and an effective amount of a quinoline derivative of the formula I as defined in claim 2.

9. A herbicidal composition containing inert additives and an effective amount of a quinoline derivative of the formula I as defined in claim 3.

10. A herbicidal composition containing inert additives and an effective amount of a quinoline derivative of the formula I as defined in claim 4.

11. A herbicidal composition containing inert additives and an effective amount of a quinoline derivative of the formula I as defined in claim 5.

12. A process for combating the growth of unwanted plants, wherein the unwanted plants and/or their location are treated with a herbicidally effective amount of a composition as defined in claim 8.

13. A process for combating the growth of unwanted plants, wherein the unwanted plants and/or their location are treated with a herbicidally effective amount of a composition as defined in claim 9.

14. A process for combating the growth of unwanted plants, wherein the unwanted plants and/or their location are treated with a herbicidally effective amount of a composition as defined in claim 10.

15. A process for combating the growth of unwanted plants, wherein the unwanted plants and/or their location are treated with a herbicidally effective amount of a composition as defined in claim 11.

* * * * *